United States Patent [19]

Linkow

[11] 4,420,305

[45] Dec. 13, 1983

[54] OBLIQUE ORAL IMPLANT

[76] Inventor: Leonard I. Linkow, 1530 Palisade Ave., Fort Lee, N.J. 07024

[21] Appl. No.: 418,043

[22] Filed: Sep. 14, 1982

[51] Int. Cl.³ .............................................. A61C 13/00
[52] U.S. Cl. .................................................. 433/176
[58] Field of Search ................ 433/173, 174, 175, 176

[56] References Cited

U.S. PATENT DOCUMENTS 3,465,441 9/1969 Linkow ................................ 433/176
3,777,402 12/1973 Roberts ................................ 433/176

Primary Examiner—Robert Peshock

Attorney, Agent, or Firm—Darby & Darby

[57] ABSTRACT

An oral implant for permanently implanting an artificial tooth supporting structure in a jawbone is adapted for use at a location where the jawbone is insufficient to support an implant blade. This implant includes a remote blade which is positioned into the jawbone at a location remote from the position where the artificial tooth is to be fixed and at a position where there is sufficient bone structure to support it. At least one post is positioned at the location where the artificial tooth is to be mounted. A cross-connecting structure connects the post and the remote blade.

4 Claims, 4 Drawing Figures

OBLIQUE ORAL IMPLANT

BACKGROUND OF THE INVENTION

This invention relates to oral implants and, more particularly, to oral implants for use where there is extensive bone deterioration at the jawbone location where an implant is desired.

Oral implants are used to mount artificial teeth where there is insufficient natural tooth structure for a conventional tooth bridge. These implants may be of the endosteal type which include the pin and spiral screw implants disclosed in U.S. Pat. No. 3,499,222 which issued to the present inventor and his associates. These are inserted directly into the jawbone at the ridge crest. Other endosteal implants include the blade types described in U.S. Pat. Nos. 3,465,441, 3,729,825 and 3,849,888, all issued to the present inventor and his associates.

All of the endosteal implants include a blade or screw adapted to be seated in a groove or tapped hole, respectively, in the patient's jawbone. One or more posts extend from the blade or screw and are used to mount the artificial tooth or teeth. To locate the implant, an incision is made in the fibromucosal tissue at the ridge crest along the endendulous span involved. The tissue is then reflected to expose the jawbone. A groove is made in the jawbone, if a blade is to be used, or a hole is tapped and threaded in the bone if a screw type implant is used. Next, the implant is inserted in the jawbone opening and the tissue is sutured about it. After a period of time, the bone in the opening grows and permanently fixes the implant.

In order for an implant to properly mount an artificial tooth, it must be positioned adjacent neighboring teeth and opposite mating teeth along the occusal plane. Under ordinary circumstances, the jawbone at the positioned where the implant is required is sufficient to permit the groove to be made therein so that the implant can be rigidly positioned. However, for various reasons, some patients suffer severe deterioration of the bone at the exact location where the implant is needed. When this is the condition an implant is contraindicated.

SUMMARY OF THE INVENTION

The present invention is directed to an oral implant for use in situations where severe bone deterioration at the implant location would normally prohibit such a device. This object is accomplished by constructing the implant so that its blade and post are remote from each other and are connected by a cross structure.

In an illustrative embodiment of the invention, the blade is inserted in a conventional manner into healthy bone adjacent the position where there has been deterioration. The post is supported at the proper implant location, remote from the blade, by a connecting structure. This structure may be a single connecting strut, a pair cross-connecting struts which form a triangular structure or a plate which conforms to the bone structure. Regardless of the technique used, the post is positioned in the proper location for correctly-aligned teeth without cross bite, and the blade is secured in a sufficient thickness of bone.

BRIEF DESCRIPTION OF THE DRAWINGS

The foregoing and other features of the invention will be more readily apparent from the following detailed description and drawings of illustrative embodiments of the invention in which.

DESCRIPTION OF EXEMPLARY EMBODIMENTS

Figure 1:
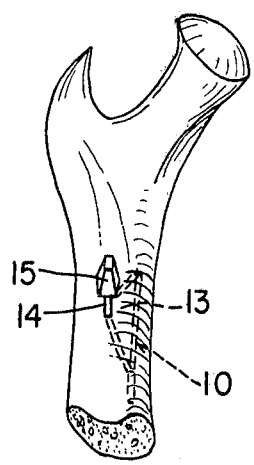
FIG. 1 is an illustrative embodiment of the invention using two cross connecting struts forming a triangular structure.
Figure 2:
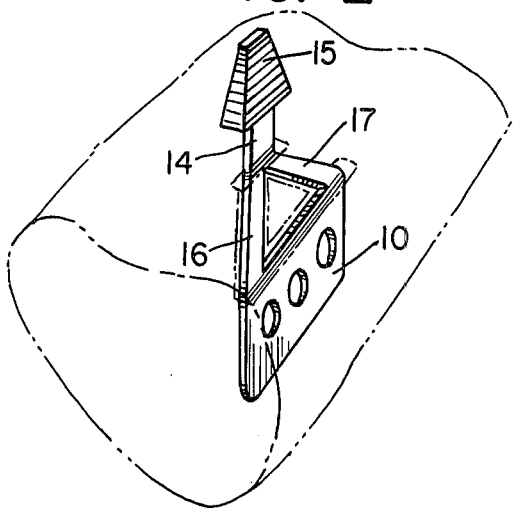
FIG. 2 is an enlarged illustrative embodiment of the invention using the two cross-connecting struts.

In FIG. 1 a portion of the jawbone is shown where there is a lack of bone height above the mandibular canal which may be due to a deep submandibular fossa below the myeoloid ridge. With such a condition, a blade implant cannot be inserted lingual to the mandibular canal. However, by using the implant shown in that figure, it is possible to overcome this difficulty. This implant has a support or blade portion 10 which is driven into a deep groove made in the external oblique ridge. Extending from the top of the blade are two struts 16, 17 that extend from the mesial and distal ends of the shoulder of the blade 10 toward the lingual surface. These struts meet at the lingual neck 14 to form a triangle as best shown in FIG. 2. The lingual neck is in turn connected to a post 15 conventionally used for supporting artificial teeth. The blade itself may be vented as shown in U.S. Pat. No. 3,849,888.

In order to prevent cross bite from occurring, which would be undesirable for the occlusion, shallow grooves are made from the end of the shoulder of the blade in a lingual direction and at angles to the shoulder of the blade. The connecting struts 16, 17 sit sits within these shallow grooves which are also at angles to the groove for the blade which is made buccal to the canal along the external oblique ridge. Because of the support provided by the shallow grooves, the post 14, which is at the lingual end of the struts, is held in proper position for occlusion with the opposing teeth.

Figure 3:
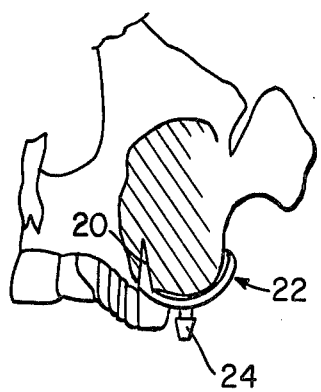
FIGS. 3 and 4 show a front and side view of an embodiment of the invention using a perforated plate for connecting the blade to the obliquely-positioned post.
Figure 4:
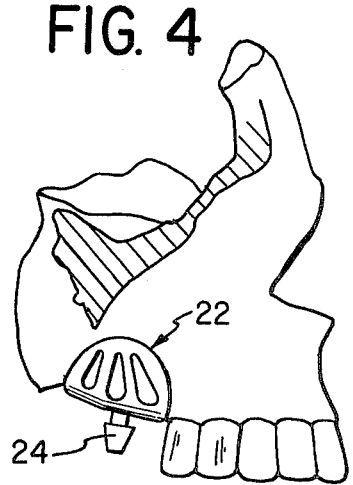

FIGS. 3 and 4 show a front view and side view of a maxillary jawbone with a subperiosteal-endosteal implant. This implant is used with its blade portion 20 inserted directly into the palatal cortex at a position which prevents perforation into a low flaring maxillary sinus. The subperiosteal portion 22, which connects the blade to the post 24 and which is preferably constructed of very thin titanium, is swedged and molded to fit simply over the remainder of the alveolar crest from the palatal cortex to the buccal aspect of the ridge. It is also closely adapted to the denser bone representing the zygomatic arch. The titanium plate is perforated to encourage its retention by tissue growth through the perforations. Also its very thin structure permits it to be shaped to the bone.

As with the previous embodiments, the blade is inserted into good thick bone material while the post is at a remote location which is in line with the rest of the patient's teeth, but which is in an area where the blade of the implant could not be inserted effectively.

While the invention has been particularly shown and described with reference to preferred embodiments thereof, it will be understood by those skilled in the art that various changes in form and details may be made therein without departing from the spirit and scope of the invention.

What is claimed is:

1. An oral implant for permanently implanting an artificial tooth supporting structure in a jawbone at a certain location along the plane of occlusion where the jawbone is insufficient to permit the insertion of an implant blade, comprising:
   a remote blade adapted for positioning into the jawbone at a location remote buccal-lingually from the certain location and at a position wherein there is sufficient bone structure to support it;
   at least one post at the certain location along the plane of occlusion, said post being adapted for mounting an artificial tooth; and
   cross-connecting structure extending buccal-lingually for connecting the post and the remote blade.

2. An oral implant as claimed in claim 1 wherein the cross-connecting structure comprises two struts extending from the mesial and distal ends of the blade, respectively, toward a base of the post and meeting to form a triangular shape.

3. An oral implant as claimed in claim 1 wherein the cross-connecting structure is a perforated plate adapted to confirm to a jawbone portion beneath it.

4. An oral implant as claimed in claim 3 wherein the blade is adapted to be inserted into the palatal cortex and the cross-connecting perforated plate is a thin metal plate extending from the blade to the post and adapted to be molded over the alveolar crest from the palatal cortex to the buccal aspect to the ridge, said plate further being adapted to extend beyond the ridge to the zygomatic arch.

* * * * *